United States Patent
Wu et al.

(10) Patent No.: US 11,097,051 B2
(45) Date of Patent: Aug. 24, 2021

(54) METHODS AND APPARATUS FOR DETECTING AND REACTING TO INSUFFICIENT HYPOGLYCEMIA RESPONSE

(71) Applicant: MEDTRONIC MINIMED, INC., Northridge, CA (US)

(72) Inventors: Di Wu, Montrose, CA (US); Rebecca K. Gottlieb, Culver City, CA (US); Benyamin Grosman, Valley Village, CA (US); Anirban Roy, Agoura Hills, CA (US); Neha J. Parikh, West Hills, CA (US); Ohad Cohen, Kiryat Uno (IL)

(73) Assignee: Medtronic MiniMed, Inc., Northridge, CA (US)

( * ) Notice: Subject to any disclaimer, the term of this patent is extended or adjusted under 35 U.S.C. 154(b) by 429 days.

(21) Appl. No.: 15/410,611

(22) Filed: Jan. 19, 2017

(65) Prior Publication Data
US 2018/0126073 A1    May 10, 2018

Related U.S. Application Data

(60) Provisional application No. 62/417,843, filed on Nov. 4, 2016.

(51) Int. Cl.
*A61M 5/172*    (2006.01)
*A61B 5/145*    (2006.01)
(Continued)

(52) U.S. Cl.
CPC ....... *A61M 5/1723* (2013.01); *A61B 5/14532* (2013.01); *A61M 5/14244* (2013.01);
(Continued)

(58) Field of Classification Search
CPC .. A61M 2230/201; A61M 2005/14208; A61M 2205/50; A61M 2205/581;
(Continued)

(56) References Cited

U.S. PATENT DOCUMENTS 3,631,847 A    1/1972   Hobbs, II
4,212,738 A    7/1980   Henne
(Continued)

FOREIGN PATENT DOCUMENTS

DE    4329229    3/1995
EP    0319268    11/1988
(Continued)

OTHER PUBLICATIONS

PCT Search Report (PCT/US02/03299), dated Oct. 31, 2002, Medtronic Minimed, Inc.
(Continued)

*Primary Examiner* — Kami A Bosworth
(74) *Attorney, Agent, or Firm* — Shumaker & Sieffert, P.A.

(57) ABSTRACT

A method for providing blood glucose data is provided. In response to a suspension of a continuous basal insulin delivery, by an insulin delivery pump, the method identifies a condition indicating continuing hypoglycemia that continues when basal insulin delivery is suspended; and performs an action, by the insulin delivery pump, based on identifying the condition.

10 Claims, 11 Drawing Sheets

(51) Int. Cl.
*G16H 50/20* (2018.01)
*G16H 20/17* (2018.01)
*G16H 50/50* (2018.01)
*G16H 40/63* (2018.01)
*A61M 5/142* (2006.01)

(52) U.S. Cl.
CPC ............. *G16H 20/17* (2018.01); *G16H 40/63* (2018.01); *G16H 50/20* (2018.01); *G16H 50/50* (2018.01); *A61M 2005/14208* (2013.01); *A61M 2205/50* (2013.01); *A61M 2205/581* (2013.01); *A61M 2205/583* (2013.01)

(58) Field of Classification Search
CPC ............ A61M 2205/583; A61M 5/003; A61M 5/1723; A61M 2005/1726; A61M 2205/3303; A61M 2230/005; A61B 5/14532; A61B 5/1723; A61B 5/14244; A61B 5/14248
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tackund et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tackund et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |

(56) References Cited

U.S. PATENT DOCUMENTS

| | | | |
|---|---|---|---|
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,833,157 B2 | 11/2010 | Gottlieb et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0173406 A1* | 8/2006 | Hayes ............... A61B 5/14532 604/67 |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088271 A1 | 4/2007 | Richards |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2011/0313390 A1 | 12/2011 | Roy et al. |
| 2014/0039383 A1* | 2/2014 | Dobbies ............... G16H 40/63 604/66 |
| 2014/0221966 A1* | 8/2014 | Buckingham ..... A61M 5/14244 604/504 |
| 2015/0157793 A1 | 6/2015 | Kovelman |
| 2015/0157796 A1* | 6/2015 | Dejournett ........... A61B 5/4839 604/503 |
| 2016/0228641 A1* | 8/2016 | Gescheit ........... A61M 5/14248 |
| 2018/0055452 A1* | 3/2018 | Breton ................ G16H 40/67 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin infusion in Type I Diabetes. Diabetes Care, vol. 19, No. 4, 324-327.

Boland E (1993). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

(56) References Cited

OTHER PUBLICATIONS

Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive insulin Therapy for Treatment of Type I Diabetes. Diabetes Care, vol. 13, No. 12, pp. 1265-1283.
Kulkami K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files./506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 insulin Pump User's Guide.
(MiniMed, 1998). MiniMed 507C insulin Pump User's Guide.
(MiniMed International; 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and In Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analylica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapienien, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian. D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.

(56) References Cited

OTHER PUBLICATIONS

Morff, Robert J. et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Navel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, el al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-134.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators. vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

Office Action from counterpart Canadian Application No. 3,040,537, dated Feb. 9, 2021, 4 pp.

\* cited by examiner

METHODS AND APPARATUS FOR DETECTING AND REACTING TO INSUFFICIENT HYPOGLYCEMIA RESPONSE

CROSS-REFERENCE TO RELATED APPLICATION

This application claims the benefit of U.S. provisional patent application Ser. No. 62/417,843, filed Nov. 4, 2016.

TECHNICAL FIELD

Subject matter disclosed herein relates to monitoring and/or controlling blood glucose levels in patients.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

BRIEF SUMMARY

Some embodiments of the present disclosure provide a method for providing blood glucose data. In response to a suspension of a continuous basal insulin delivery, by an insulin delivery pump, the method identifies a condition indicating continuing hypoglycemia that continues when basal insulin delivery is suspended; and performs an action, by the insulin delivery pump, based on identifying the condition.

Some embodiments of the present disclosure provide a system for providing blood glucose data. The system includes an insulin delivery pump comprising a glucose delivery system, a glucagon delivery system, an insulin delivery system, and a glucose sensor system; and a controller comprising a system memory element and at least one processor, the controller communicatively coupled to the insulin delivery pump, and the controller configured to: in response to a suspension of a continuous basal insulin delivery, by the insulin delivery pump, identify a condition indicating continuing hypoglycemia that continues when basal insulin delivery is suspended; and initiate performance of an action, by the insulin delivery pump, based on identifying the condition.

Some embodiments of the present disclosure provide an insulin delivery pump comprising a non-transitory, computer-readable medium containing instructions thereon, which, when executed by a processor, perform a method. The method predicts a hypoglycemic condition that is not rectifiable by suspending a continuous basal insulin delivery; and presents an alert, based on the hypoglycemic condition.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
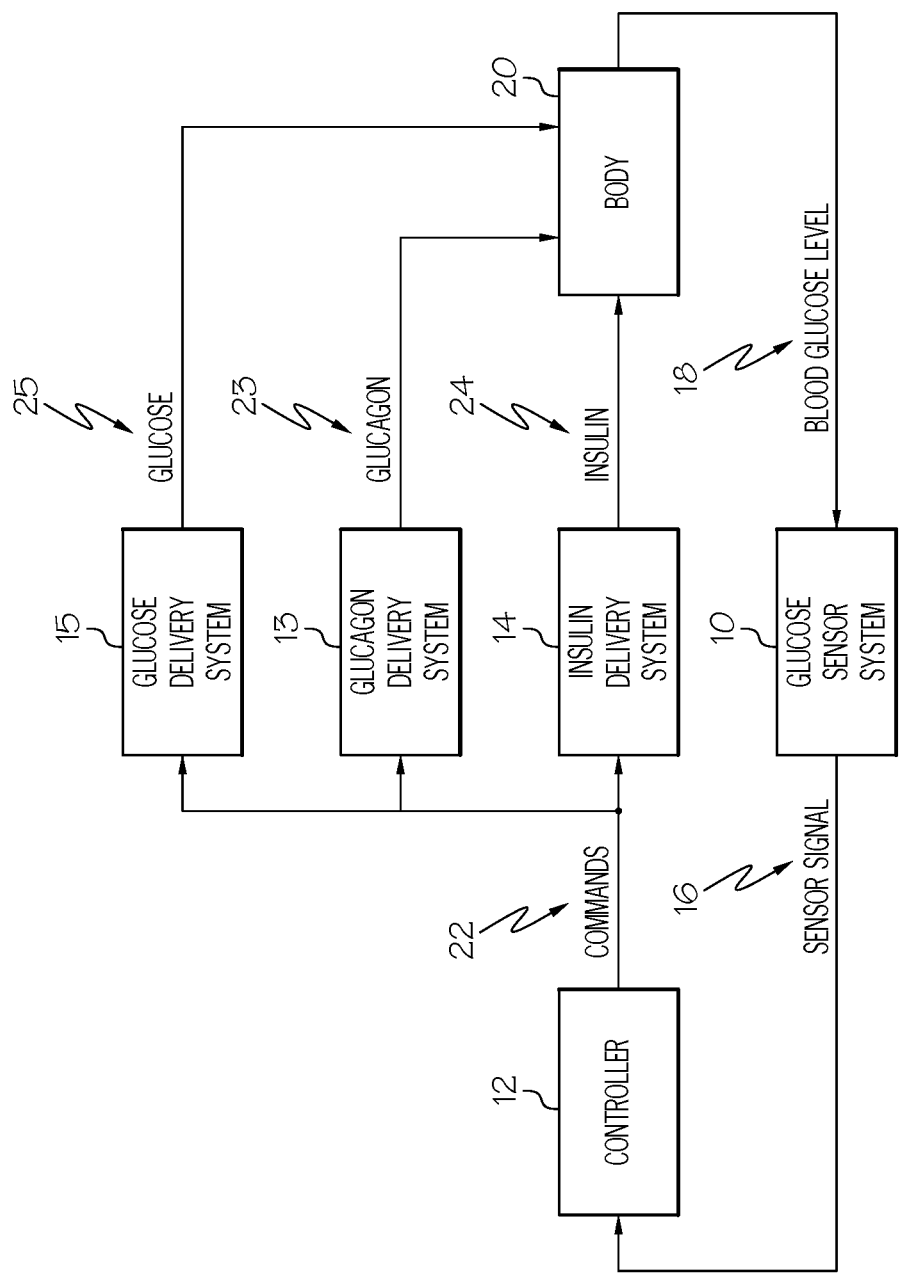
FIG. 1 is a block diagram of a closed loop glucose control system in accordance with an embodiment.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to apparatus and methods for predicting an insufficient response, by an insulin delivery pump, to a hypoglycemic event. An insulin delivery pump normally operates to: (i) provide a continuous delivery of basal insulin to a user of the pump, and (ii) provide a bolus (i.e., a single dose of a drug or other medicinal preparation given all at once) of insulin, on an as-needed basis. Under normal operation, the insulin delivery pump detects anticipated hypoglycemic events and responds by suspending the continuous basal insulin delivery, in an attempt to prevent an upcoming hypoglycemic event. In certain circumstances, such suspension of basal insulin delivery is insufficient to prevent the hypoglycemic event. In this scenario, the insulin delivery pump can first predict the anticipated insufficient response, and second perform an action based on the anticipated insufficient response. Such actions may include presenting an alert, providing information for patient education, and/or providing a glucagon injection via the insulin delivery pump.

Certain terminologies are used with regard to the various embodiments of the present disclosure. A glucose trend is the rate of change for a series of blood glucose values, acquired over a period of time, from a single patient or user of an sensor augmented insulin delivery pump. Hypoglycemia is a low level of glucose in the bloodstream of the patient or user of the insulin delivery pump, and may be generally associated with blood glucose values below 70 milligrams per deciliter (mg/dL). An insulin on board (IOB) value is descriptive of the residual insulin activity following a bolus of insulin provided by the insulin delivery pump. A total daily dose (TDD) value is a quantity of insulin required by the user in a twenty-four (24) hour period. A missed hypoglycemic event is an occurrence of a time period of hypoglycemia that is not prevented, avoided, or corrected by suspension of a continuous delivery of basal insulin.

In an exemplary glucose control system environment, blood-glucose measurements may be employed in a closed loop infusion system for regulating a rate of fluid infusion into a body. In particular embodiments, a control system may be adapted to regulate a rate of insulin, glucagon, and/or glucose infusion into a body of a patient based, at least in part, on a glucose concentration measurement taken from a body (e.g., from a glucose sensor and/or metered blood glucose measurement). In certain implementations, such a system may be designed to model a pancreatic beta cell (β-cell). Here, such a system may enable a patient to control an infusion device for releasing insulin, glucagon or glucose into the patient's body for effective blood glucose management. Here, such a system may be adapted to control infusion of insulin and/or glucagon so as to control/maintain a patient's blood glucose within a target range, thus reducing the risk that a patient's blood glucose level transitions to dangerous extreme levels in the absence of patient action.

According to certain embodiments, examples of closed-loop systems as described herein may be implemented in a hospital environment to monitor and/or control levels of glucose in a patient. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

In a particular embodiment of a closed-loop system, such a system may be adapted to control infusion of insulin and/or glucagon so as to control/maintain a patient's blood glucose within a target range, thus reducing the risk that a patient's blood glucose level transition to dangerous extreme levels. Again, such a mechanism may reduce the risk of hypoglycemia and hyperglycemia if a patient, non-medical professional or medical professional is not fully attentive to providing inputs to the system for effective glycemic management.

According to an embodiment, depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dL, which is in the normal glycemic range. Alternatively, target or set-point glucose level may be fixed at 120 mg/dL. In yet another alternative, a target or set-point blood glucose concentration may vary over time depending on particular patient conditions. It should be understood, however, that these are merely examples of a target or set-point blood glucose concentration, and claimed subject matter is not limited in this respect.

According to an embodiment, a closed-loop system may be employed to maintain a patient's glucose level in a range about a predetermined set-point or target level as described in U.S. patent application Ser. No. 12/820,944, filed on Jun. 22, 2010, and assigned to the assignee of claimed subject matter. Here, insulin may be infused to the patient at a predetermined basal rate while the patient's glucose level is within the predetermined range. If the glucose level escapes that range, a different infusion rate may be applied based, at least in part, on the predetermined set-point or target level. For example, if the patient's glucose level exceeds the range, an insulin infusion rate may be increased. In another example, if the patient's glucose level falls below a particular level, an insulin infusion rate may be reduced from the predetermined basal rate. Of course, these are merely examples of how the insulin infusion rate may be changed if a patient's glucose level escapes a particular range, and claimed subject matter is not limited in this respect.

By maintaining a predetermined basal insulin infusion rate while the glucose level is within a target range, extreme glycemic variations may be reduced or avoided altogether. This may provide a patient with improved glycemic control in circumstances in which they would otherwise be exposed to undesirable extremes of glycemia. Here, while such a patient may remain in control of insulin infusion decisions, particular embodiments may respond automatically in the absence of particular patient action (e.g., forgetting to bolus insulin to cover a meal) to prevent blood glucose from reaching extreme levels.

A controller may employ any one of several control techniques for computing determining commands for a pump in attempt to maintain a patient's observed blood glucose concentration within a target range. For example, a controller may employ a proportional-integral-derivative (PID) control algorithm in conjunction with controlling a patient's blood glucose level within a particular range as described in U.S. patent application Ser. No. 12/820,944, filed on Jun. 22, 2010, and assigned to the assignee of claimed subject matter. Here, such a PID algorithm may, at least in part, predict a level of blood glucose in a patient at some set time in the future and, based on such a prediction, compute commands to be provided to an infusion pump. While such a PID algorithm may provide an effective technique for maintaining a patient's blood glucose within a target range, a PID algorithm may not fully consider health risks of a blood glucose level being outside of a target range from time to time.

Briefly, according to an embodiment, a predicted blood glucose level of a patient based, at least in part, on past blood glucose measurements and control signals to be applied to at least one infusion pump. A cost expression is determined based, at least in part, on the predicted blood glucose level. The control signals to be applied to the at least one infusion pump may then be affected so as to achieve a cost value according to said cost expression. In one particular implementation, that cost expression is determined based, at least in part, on a predicted duration that that the blood glucose is to be outside of a target range over some interval in the future. Accordingly, the control signals applied to the at least on infusion pump may be responsive to risks associated with the patient's blood glucose level being outside of the target range.

As pointed out above, insulin infusion therapy may be controlled, at least in part, by techniques for predicting a patient's blood glucose level or glycemic state at some point or time in the future (e.g., using a PID algorithm as discussed above). In this context, a "glycemic state" may be determined based on one or more factors such as, for example, a blood glucose concentration. Algorithms may receive measurements or observations of a patient's blood glucose concentration from, for example, a continuous blood glucose monitoring device processing signals from a blood-glucose sensor inserted into subcutaneous tissue. However, merely predicting a blood glucose level at some time in the future may have limited utility in applying a therapy to a patient. For example, systems that predict a blood glucose concentration at some time in the future may merely provide a single blood glucose level prediction for a single instance in the future, and may not fully characterize a patient's glycemic state, or transitions from an initial glycemic state to a possible future glycemic state, for the purpose of applying an appropriate therapy.

In another implementation, insulin infusion therapy may be affected or controlled by a prediction of a duration of time until a patient's current glycemic state or blood glucose level is to reach a target blood glucose concentration or glycemic state. Among other factors, this predicted duration may be based, at least in part, on observations of the patient's current blood glucose level according to signals received from a blood-glucose sensor. This predicted duration may then be used for determining how the patient's therapy may be altered by, for example, changing a rate of insulin infusion.

Predicting a duration of time until a patient is to reach a particular blood glucose level starting from an initial state may enable techniques for characterizing a patient's glycemic state that may not be possible with predicting the patient's blood-glucose level in the future alone. Additionally, a predicted time until a patient reaches a particular glycemic state may enable an enhanced ability to for closed-loop insulin infusion systems.

Turning now to the figures, FIG. 1 is a block diagram of an example closed-loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain exemplary embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using, e.g., a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable, a wire, a fiber optic line, RF, IR, or ultrasonic transmitters and receivers, combinations thereof, and/or the like instead of electrical traces, just to name a few examples.

Figure 2:
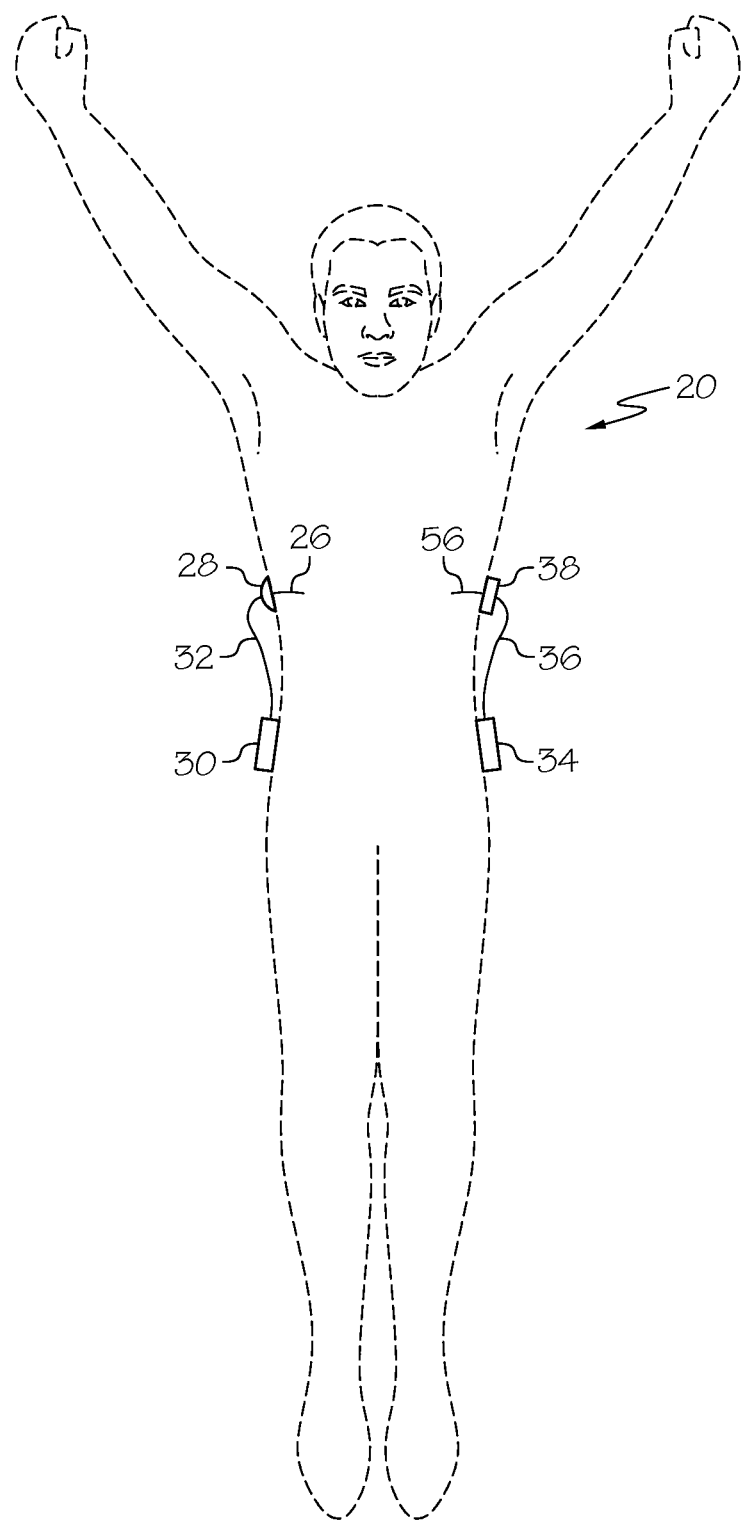
FIG. 2 is a front view of closed loop hardware located on a body in accordance with an embodiment.
Figure 3A:
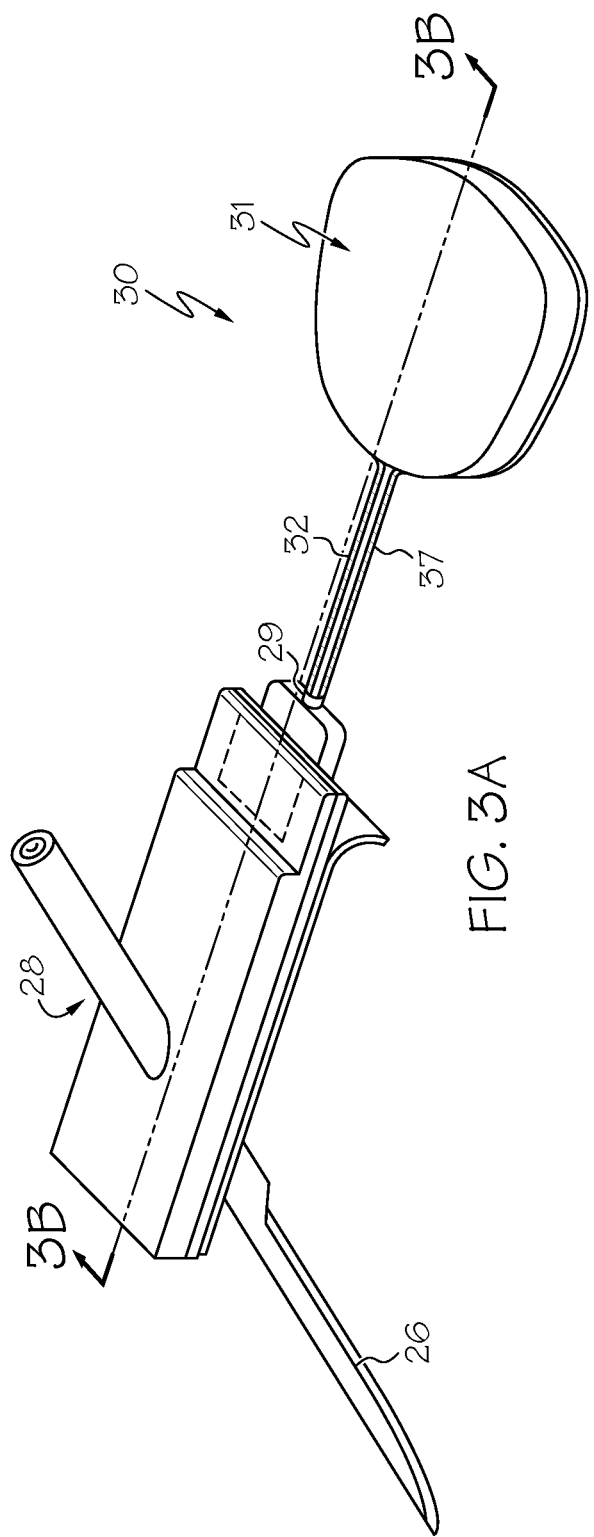
FIG. 3A is a perspective view of a glucose sensor system for use in accordance with an embodiment.
Figure 3B:
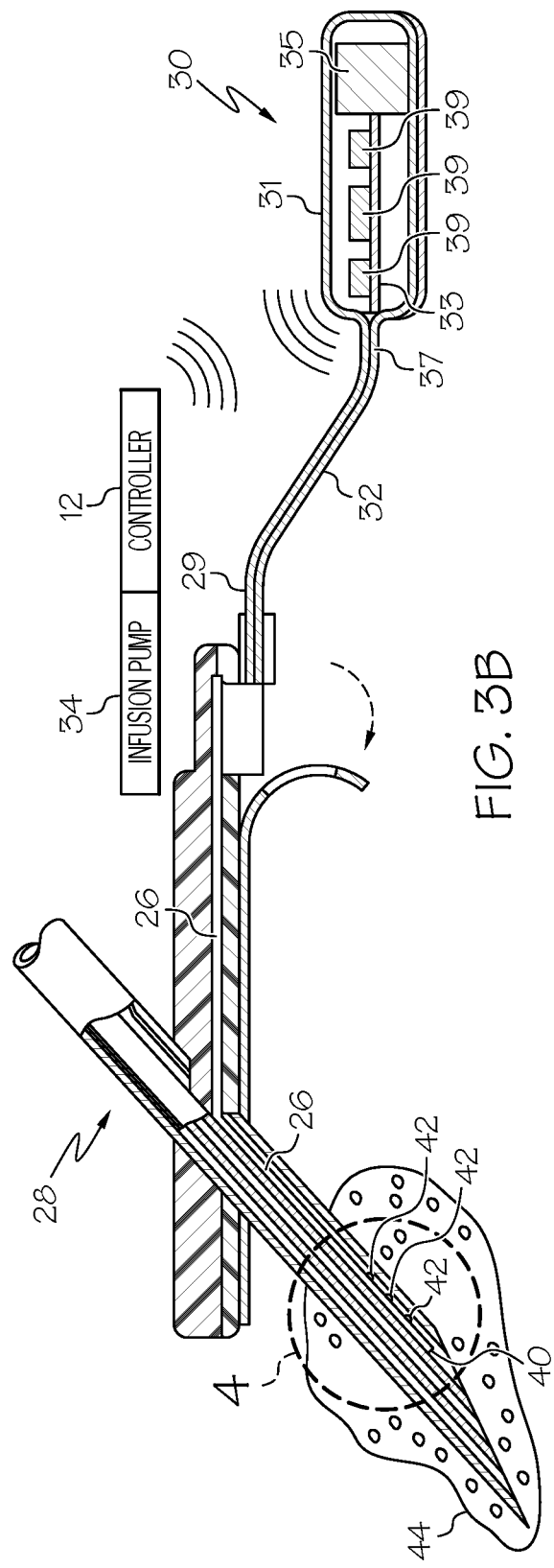
FIG. 3B is a side cross-sectional view of the glucose sensor system of FIG. 3A for an embodiment.
Figure 3C:
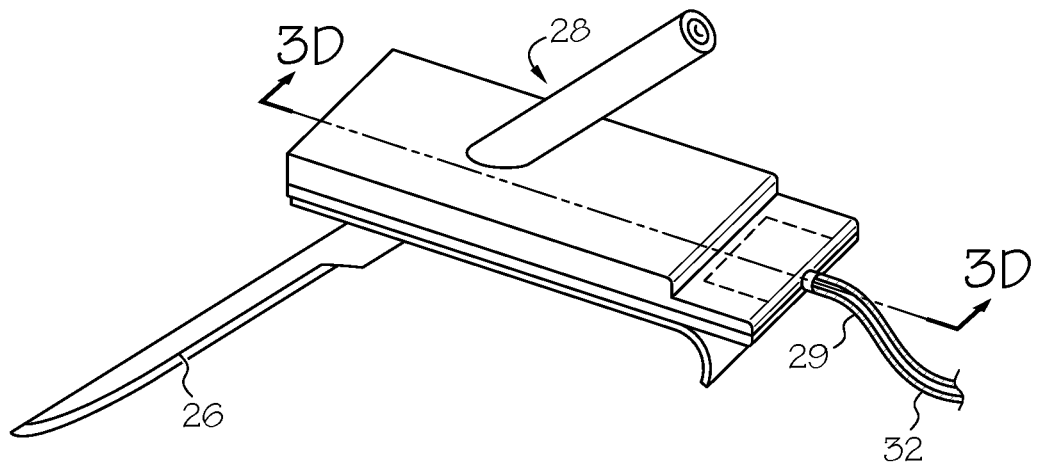
FIG. 3C is a perspective view of a sensor set of a glucose sensor system of FIG. 3A for an embodiment.
Figure 3D:
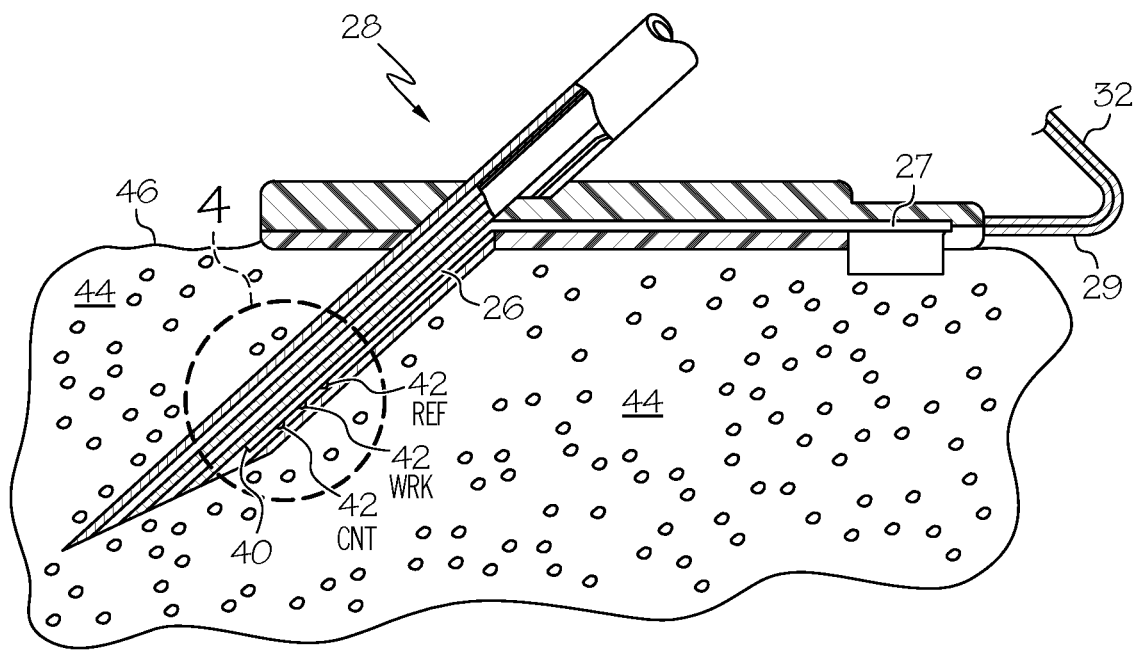
FIG. 3D is a side cross-sectional view of a sensor set of FIG. 3C for an embodiment.
Figure 4:
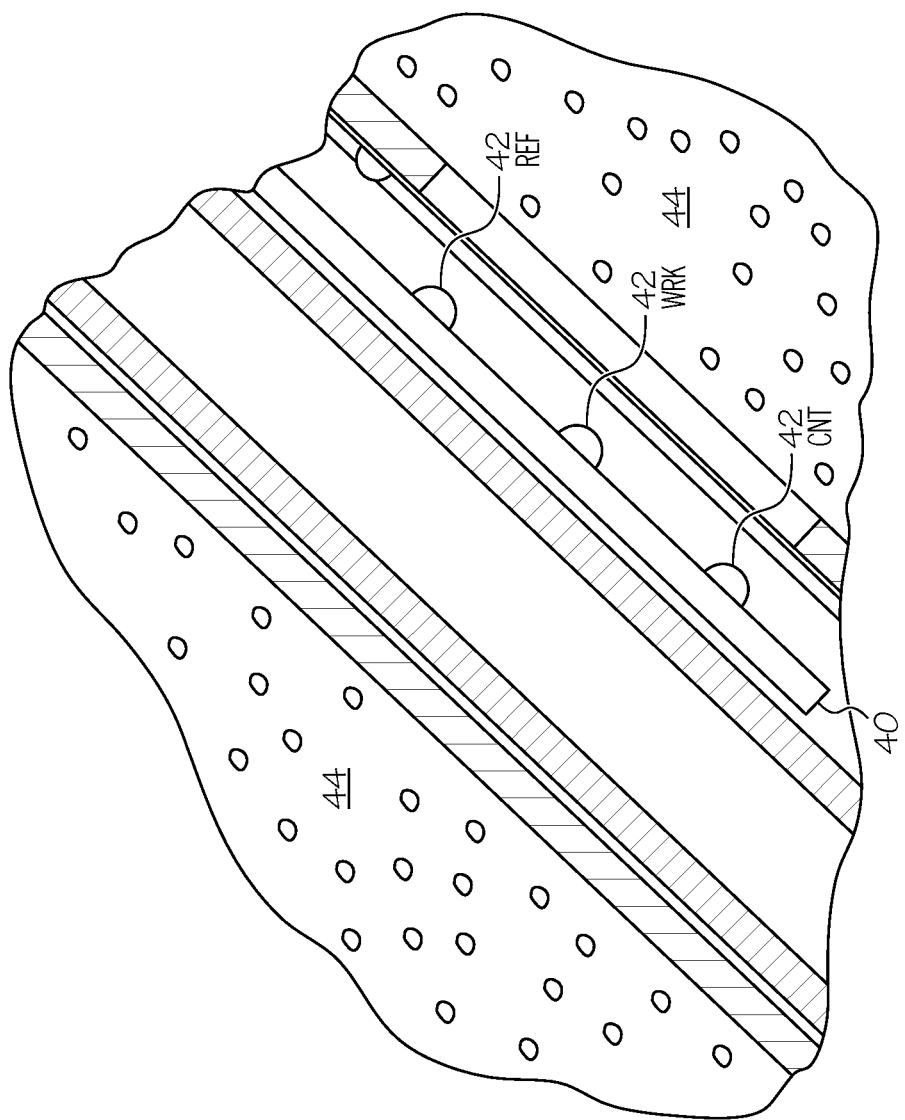
FIG. 4 is a cross sectional view of a sensing end of a sensor set of FIG. 3D for an embodiment.
Figure 5:
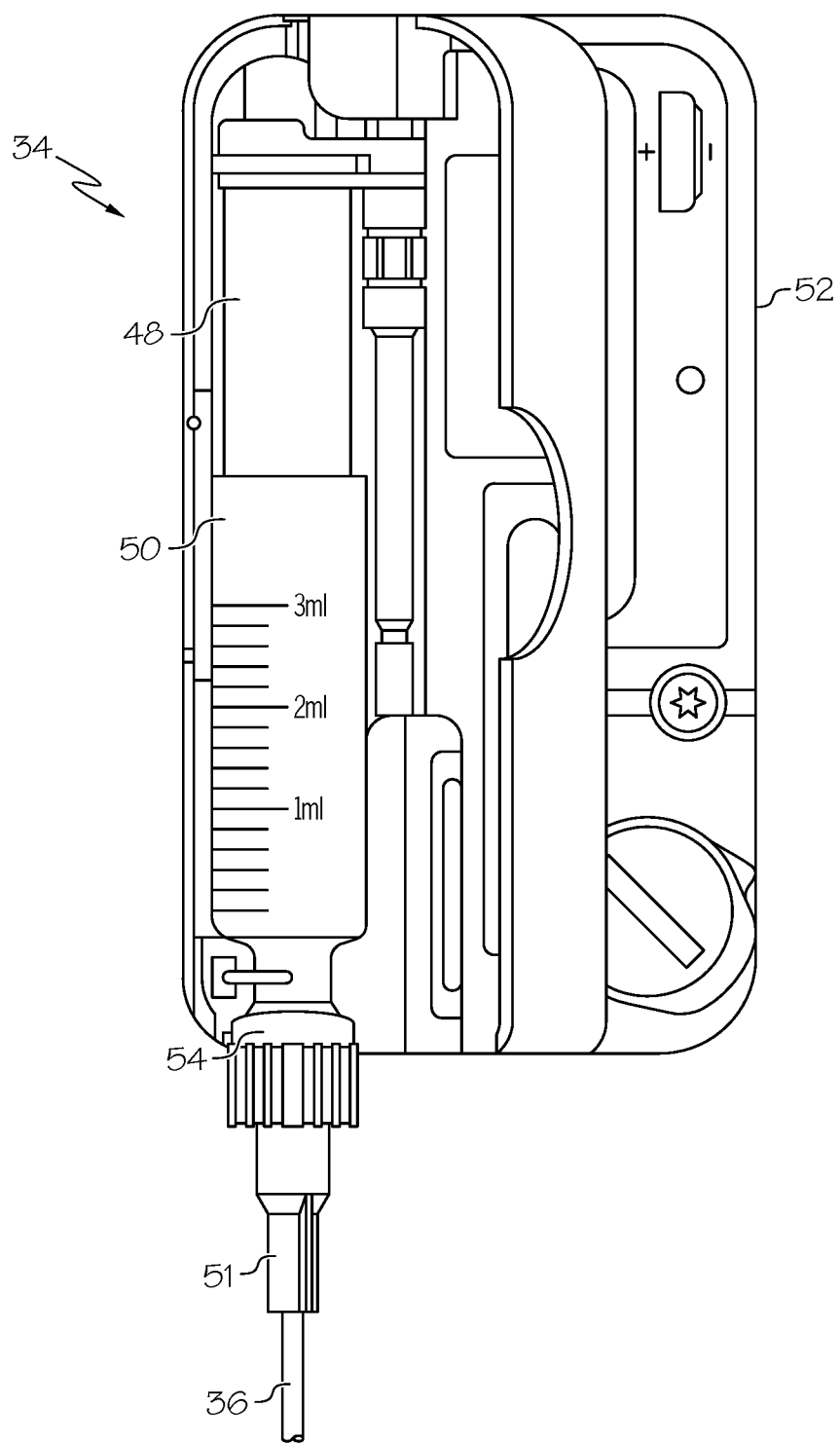
FIG. 5 is a top view of an infusion device with a reservoir door in an open position, for use according to an embodiment.
Figure 6:
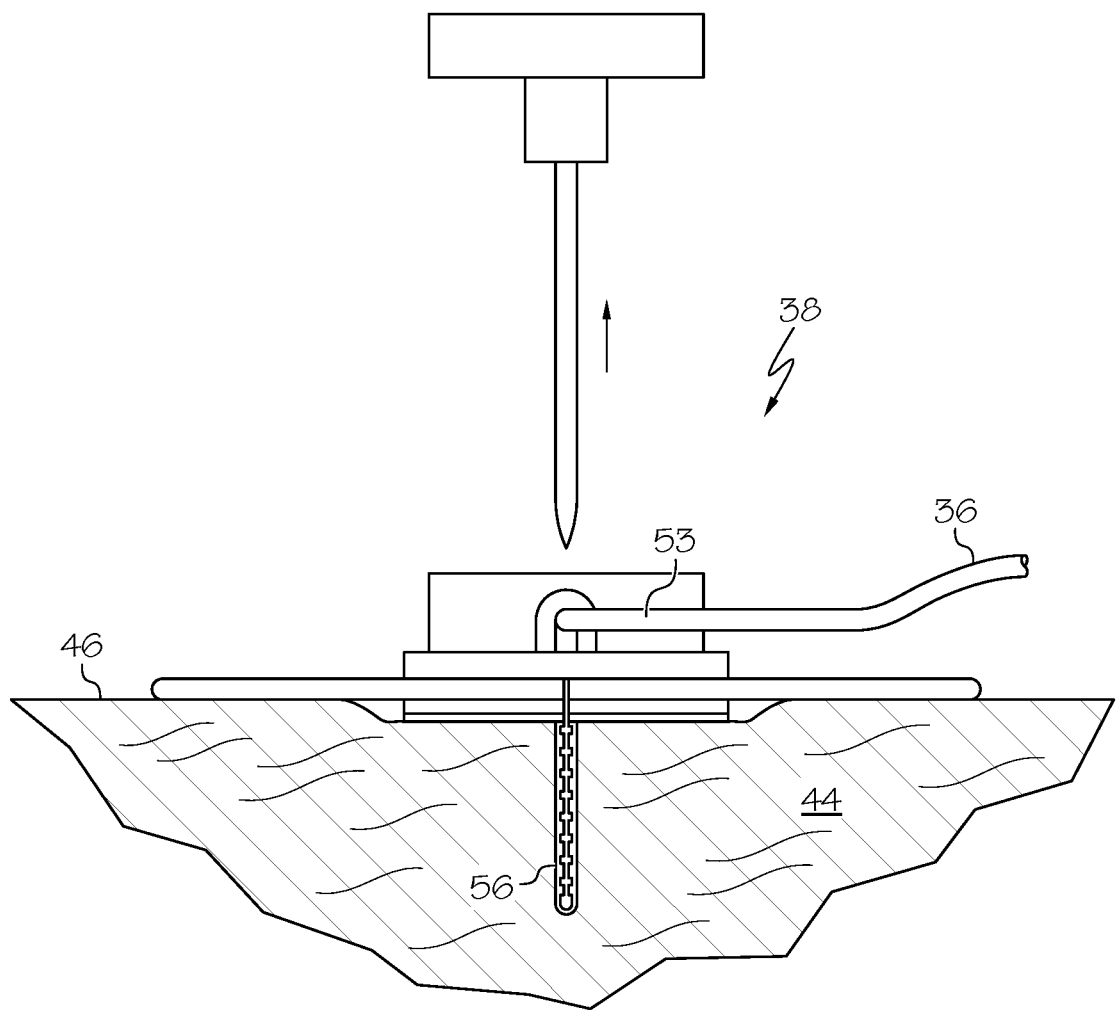
FIG. 6 is a side view of an infusion set with an insertion needle pulled out, for use according to an embodiment.

FIGS. 2-6 illustrate glucose control systems in accordance with certain embodiments. Such glucose control systems may be used, for example, in controlling a patient's glucose level about a target range as discussed above. It should be understood, however, that these are merely examples of particular systems that may be used for controlling a patient's glucose level about a target range and that claimed subject matter is not limited in this respect. FIG. 2 is a front view of closed loop hardware located on a body in accordance with certain embodiments. FIGS. 3A-3D and 4 show different views and portions of an exemplary glucose sensor system for use in accordance with certain embodiments. FIG. 5 is a top view of an infusion device with a reservoir door in an open position in accordance with certain embodiments. FIG. 6 is a side view of an infusion set with an insertion needle pulled out in accordance with certain embodiments.

Particular embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3A and 3B, telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3D and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3C and 3D. Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 1, 2, and 5, a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucagon may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 20 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 20.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Pat. No. 7,833,157; entitled "MULTILUMEN CATHETER", may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Certain examples of system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that may contribute to a sensor measurement lagging behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 7:
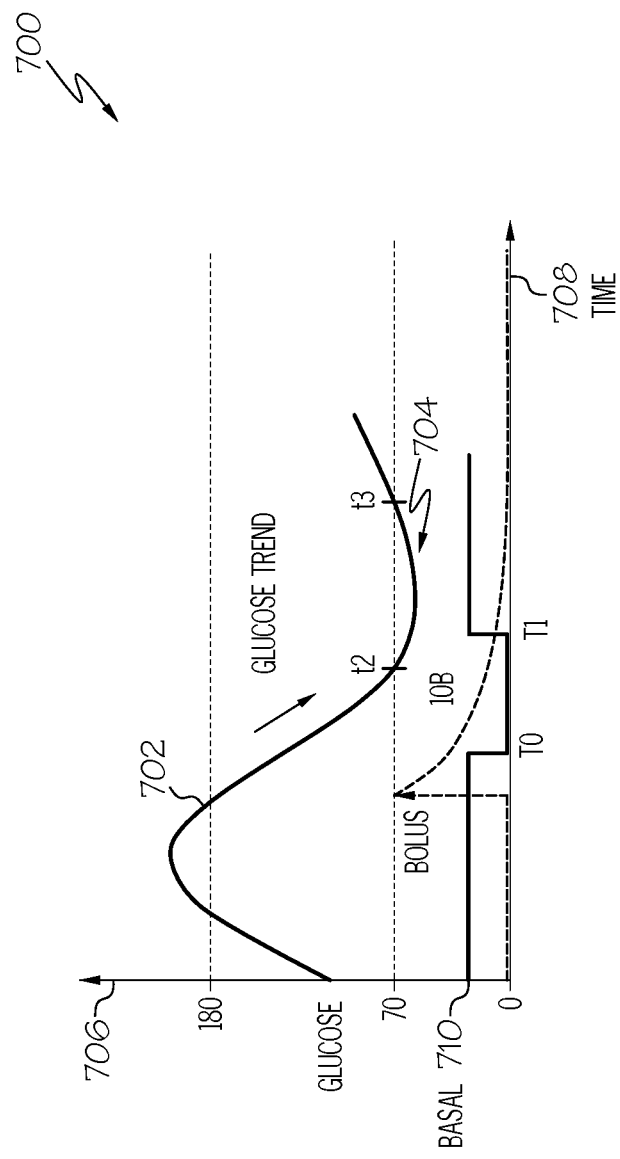
FIG. 7 is a plot of a trajectory of a blood glucose trend including a period of hypoglycemia that is not rectified by suspension of a continuous basal insulin delivery.

FIG. 7 is a plot 700 of a trajectory of a blood glucose trend 702 including a period of hypoglycemia 704 that is not rectified by suspension of a continuous basal insulin delivery. The plot 700 shows the glucose trend 702 as a plurality of blood glucose levels 706, for a particular user, over time 708. The blood glucose levels 706 associated with the glucose trend 702 are obtained by blood glucose sensors of an insulin delivery pump. As shown, the glucose trend 702 increases from the origin to a glucose level 706 above 180 milligrams per deciliter (mg/dL), and then decreases to a glucose level 706 below 70 mg/dL. The glucose levels 706 below 70 mg/dL indicate low blood glucose for a duration of time between time $t_3$ and time $t_4$ (e.g., the period of hypoglycemia 704).

The plot 700 also illustrates a continuous basal insulin delivery 710 that is suspended (i.e., the basal insulin delivery 710 stops) at time $t_0$, and remains suspended until time $t_1$. Here, the basal insulin plot is superimposed for consistency with the time scale, but is not measured according to the vertical scale. The basal insulin is plotted using Units per hour (Unit/h). The bolus insulin and insulin on board (IOB) are also plotted using Unit as the vertical scale.

The purpose of the suspension is to address the decreasing blood glucose levels 706 that are shown by the glucose trend 702. However, in this example, the glucose trend 702 continues to decrease and remains in a hypoglycemic state for a duration of time 708 (e.g., the period of hypoglycemia 704), and the suspension of the basal insulin delivery 710 at time $t_0$ did not stop the occurrence of the period of hypoglycemia 704. In this situation, the glucose trend 702 shows blood glucose levels 706 below 70 mg/dL until time $t_3$, at which point the glucose trend 702 is increasing and passes through the 70 mg/dL threshold, at which point (e.g., time point $t_3$) the period of hypoglycemia 704 has ended.

The plot 700 depicts one particular instance where suspension of the continuous basal insulin delivery 710 by itself is not enough to stop a period of hypoglycemia 704 from occurring. When this scenario occurs, additional actions may be required to prevent a period of hypoglycemia, or to rectify a current period of hypoglycemia. An insulin delivery pump may take other actions to rectify the anticipated period of hypoglycemia, in combination with the suspension of the basal insulin delivery 710. For example, the insulin delivery pump may provide a glucagon injection, or other type of blood glucose medication, or generate an alert so that a user can take additional actions (e.g., the user may choose to ingest fruit juice or blood glucose medication, in response to the alert).

Figure 8:
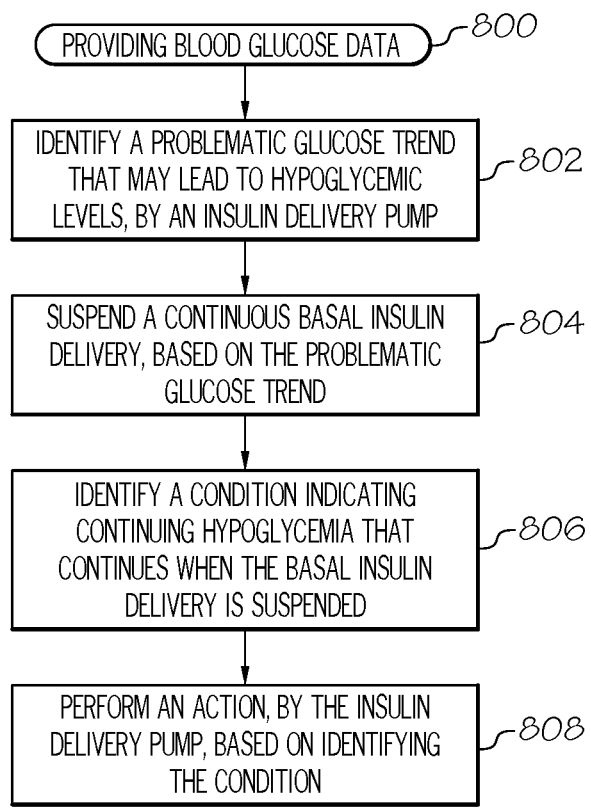
FIG. 8 is a flow chart that illustrates an exemplary embodiment of a process for providing blood glucose data.

FIG. 8 is a flow chart that illustrates an exemplary embodiment of a process 800 for providing blood glucose data. The various tasks performed in connection with process 800 may be performed by software, hardware, firmware, or any combination thereof. For illustrative purposes, the following description of process 800 may refer to elements mentioned above in connection with FIGS. 1-7. In practice, portions of process 800 may be performed by different elements of the described system. It should be appreciated that process 800 may include any number of additional or alternative tasks, the tasks shown in FIG. 8 need not be performed in the illustrated order, and process 800 may be incorporated into a more comprehensive procedure or process having additional functionality not described in detail herein. Moreover, one or more of the tasks shown in FIG. 8 could be omitted from an embodiment of the process 800 as long as the intended overall functionality remains intact.

First, the process 800 identifies a problematic glucose trend that may lead to hypoglycemic levels, by an insulin delivery pump (step 802). The insulin delivery pump is communicatively coupled to a subcutaneous sensor, and is continuously monitoring blood glucose levels of the user of the insulin delivery pump via the subcutaneous sensor (as described previously, with regard to FIGS. 1-6). In certain embodiments, the insulin delivery pump is configured to obtain blood glucose levels for the user, via the subcutaneous sensors, at timed intervals. In some embodiments, however, the insulin delivery pump may be activated to obtain blood glucose levels in response to an input user request. As the blood glucose levels are obtained, the process 800 continuously calculates a rate of change for the blood glucose levels. The rate of change for the blood glucose levels may be referred to as the glucose trend. A problematic glucose trend is a glucose trend which is decreasing at a rapid rate. In exemplary embodiments of the present disclosure, a glucose trend that is decreasing at a rapid rate may be defined as a sensor rate of change below −1 milligrams per deciliter (mg/dL), per minute.

Next, the process 800 suspends a continuous basal insulin delivery, based on the problematic glucose trend (step 804). The insulin delivery pump is configured to automatically suspend basal insulin delivery when sensor glucose levels are predicted to approach a low limit, and to resume basal insulin delivery once sensor glucose levels recover. Thus, the insulin delivery pump functions to reduce hypoglycemic events and to reduce time spent in the hypoglycemic range. Here, the process 800 predicts that sensor glucose levels will approach a low limit, based on the identified problematic glucose trend (step 802), and, in response, suspends basal insulin delivery.

The process 800 then identifies a condition indicating a continuing hypoglycemia that continues when the basal insulin delivery is suspended (step 806). One suitable methodology for identifying the condition is described below with reference to FIG. 9. A second suitable methodology for identifying the condition is described below with reference to FIG. 10. Here, the insulin delivery pump is aware of a predicted, upcoming hypoglycemic event, and the process 800 determines that the hypoglycemic event will continue after the insulin delivery pump reacts to the upcoming hypoglycemic event by suspending basal insulin delivery. In other words, the suspension of the basal insulin delivery is insufficient to prevent the period of hypoglycemia, and additional treatment is required to address the hypoglycemic event.

After identifying the condition (step 806), the process 800 performs an action, by the insulin delivery pump, based on identifying the condition (step 808). The action may include presenting an alert, by the insulin delivery pump. The alert may include an audio alert, a visual alert, or any combination thereof. Exemplary embodiments may include a "pop-up" message presented on a display of the insulin delivery pump, a voice communication informing the user of the condition, and/or an alarm that sounds when the condition is detected.

Figure 9:
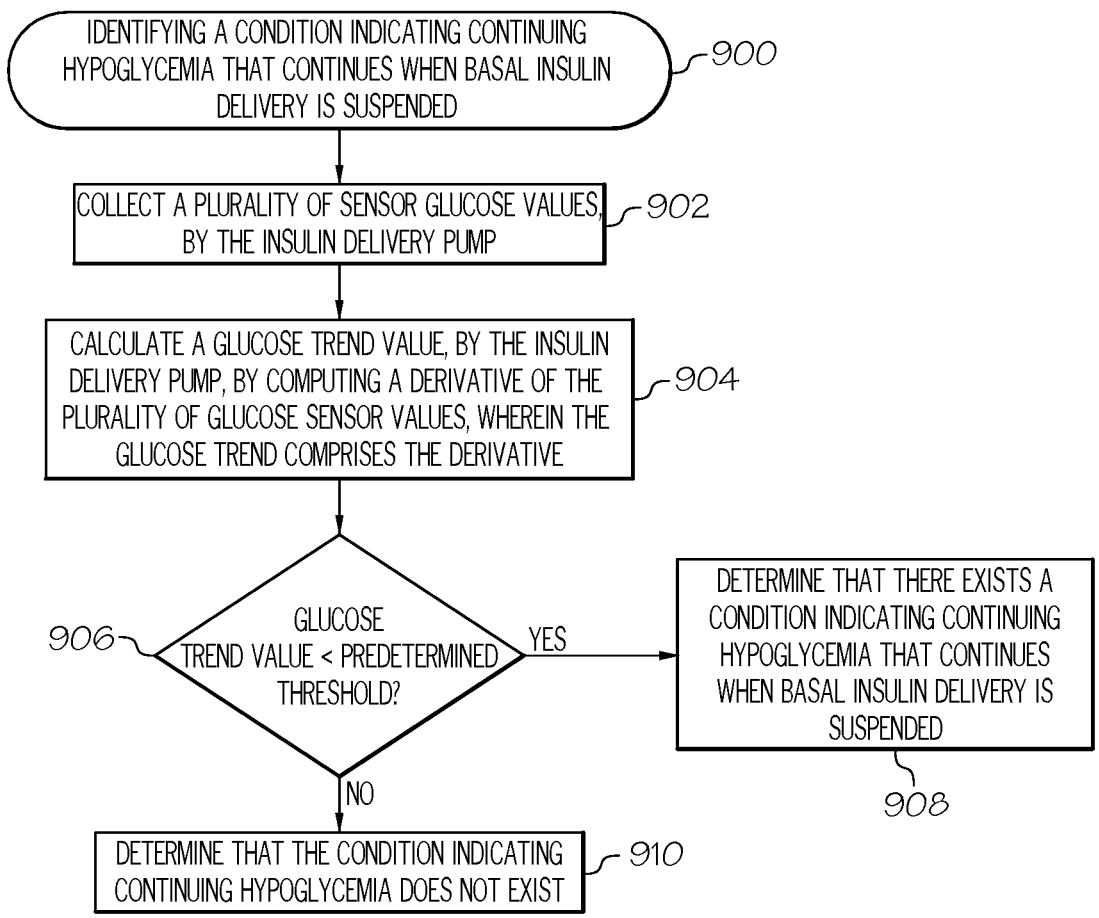
FIG. 9 is a flow chart that illustrates an exemplary embodiment of a process for identifying a condition indicating continuing hypoglycemia that continues when basal insulin delivery is suspended.

FIG. 9 is a flow chart that illustrates an exemplary embodiment of a process 900 for identifying a condition indicating continuing hypoglycemia that continues when basal insulin delivery is suspended. It should be appreciated that the process 900 described in FIG. 9 represents one embodiment of step 806 described above in the discussion of FIG. 8, including additional detail. First, the process 900 collects a plurality of sensor glucose values, by the insulin delivery pump (step 902), for purposes of determining a glucose trend which is used to detect missed hypoglycemic events. The glucose trend is one of the dominant factors of severity of impending hypoglycemia, and thus may be used to detect a hypoglycemic event during which suspension of basal insulin delivery is insufficient to prevent or rectify the hypoglycemic event. The glucose trend may also be referred to as a glucose rate of change and/or a glucose derivative.

Next, the process 900 calculates a glucose trend value by computing a derivative of the plurality of glucose sensor values, wherein the glucose trend comprises the derivative (step 904). The calculation of the derivative of the plurality of glucose sensor values is a commonly used glucose trend calculation technique that is well-known in the industry. Generally, the insulin delivery pump performs these calculations using an internally integrated controller or processor (see FIG. 1), and presents the results of the calculations via a display device communicatively coupled to the controller. In certain embodiments, the insulin delivery pump presents, via the display device, glucose trend information as one or more graphical elements (e.g., arrows). For example, one arrow pointing up indicates that the glucose trend (i.e., glucose rate of change) is greater than 1 mg/dL per minute, and one arrow pointing down indicates that the glucose trend is less than −1 mg/dL per minute. Thus, the glucose trend is generally readily available information that is provided by an insulin delivery pump.

The process 900 then determines whether the glucose trend value is less than a predetermined threshold (decision 906). The predetermined threshold is obtained by analyzing actual insulin delivery pump data, and identifying a threshold that indicates hypoglycemia, based on the analysis.

When the glucose trend value is not less than the predetermined threshold (the "No" branch of 906), the process 900 determines that the condition indicating continuing hypoglycemia does not exist (step 910). However, when the glucose trend value is less than the predetermined threshold (the "Yes" branch of 906), the process 900 determines that there exists a condition indicating continuing hypoglycemia that continues when basal insulin delivery is suspended (step 908). Here, the process 900 determines that blood glucose levels decrease to a point below a "suspension threshold" (i.e., a threshold point at which the insulin delivery pump suspends basal insulin delivery). Due to a rapid decrease in the glucose trend detected by the process 900, the process 900 predicts the existence of a condition in which blood glucose levels will continue to decrease, thereby inducing hypoglycemia.

Figure 10:
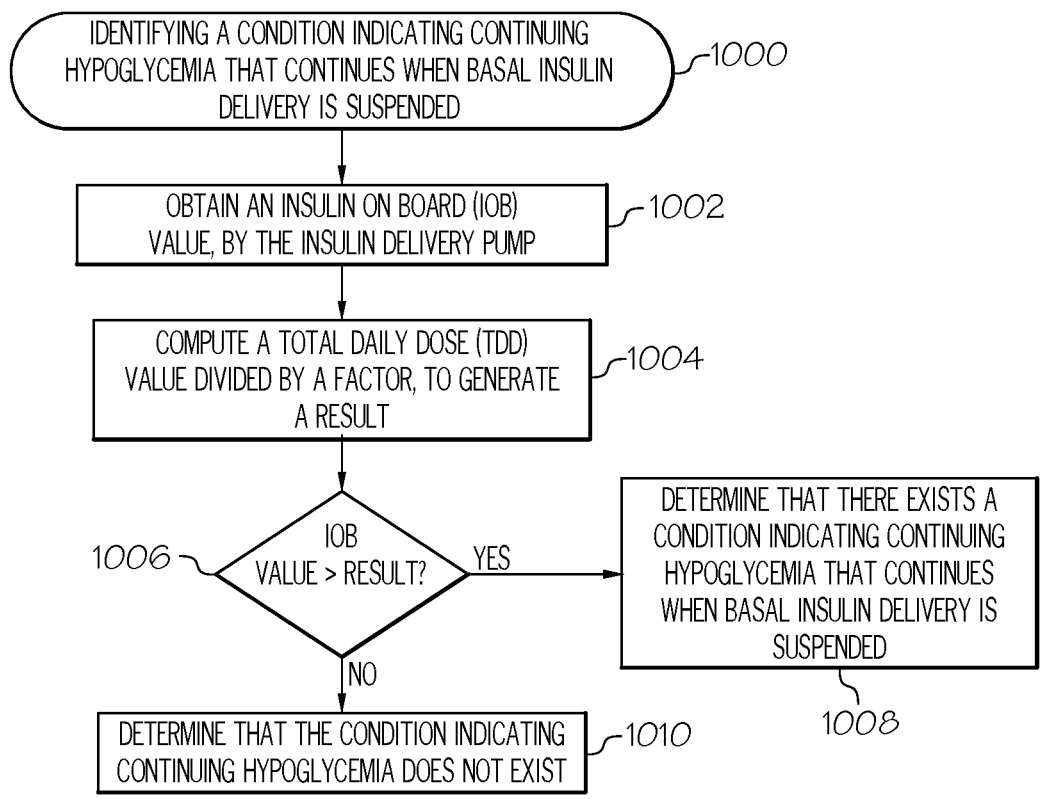
FIG. 10 is a flow chart that illustrates another exemplary embodiment of a process for identifying a condition indicating continuing hypoglycemia that continues when basal insulin delivery is suspended.

FIG. 10 is a flow chart that illustrates another exemplary embodiment of a process 1000 for identifying a condition indicating continuing hypoglycemia that continues when basal insulin delivery is suspended. It should be appreciated that the process 1000 described in FIG. 10 represents one embodiment of step 806 described above in the discussion of FIG. 8, including additional detail. The process 1000 uses glucose trend values and insulin on board (IOB) values to identify the condition indicating continuing hypoglycemia that continues when basal insulin delivery is suspended. This is because the blood glucose trend and the IOB value are two fundamental conditions that can cause a hypoglycemic event. In other embodiments, there could be other states associated with a hypoglycemic event, such as a predicted glucose value or a plasma insulin value. However, the predicted glucose value and the plasma insulin value provide the same information for analysis. Blood glucose trend values and IOB values are used because the information is readily available from a standard insulin delivery pump and require no additional calculations.

First, the process 1000 obtains an insulin on board (IOB) value, by the insulin delivery pump (step 1002), which is used to detect missed hypoglycemic events. An insulin on board (IOB) value is a quantity of insulin remaining in the body of the user following a bolus of insulin provided by the insulin delivery pump. The IOB value is one of the dominant factors of severity of impending hypoglycemia, and thus may be used to detect a hypoglycemic event during which suspension of basal insulin delivery is insufficient to prevent or rectify the hypoglycemic event. The insulin on board (IOB) value reflects the current effective insulin existing inside the body which will keep lowering blood glucose values. The higher the IOB value is, the faster blood glucose levels will drop.

Next, the process 1000 computes a total daily dose (TDD) value divided by a factor, to generate a result (step 1004). A total daily dose (TDD) value is a quantity of insulin required by the user in a twenty-four (24) hour period. TDD is a factor that reflects how sensitive the patient is to insulin. The higher the TDD value is, the more insulin the patient requires to compensate for blood glucose in the body of the patient.

The process 1000 then determines whether the IOB value is greater than the result (decision 1006). Here, the process 1000 is comparing the quantity of insulin remaining in the body (i.e., IOB) to the quantity of insulin required by the user in a 24-hour period (i.e., TDD), to predict a potential insufficient response to a hypoglycemic event. The TDD value reflects insulin sensitivity of the patient. Thus, the IOB value needs to be above the patient dependent factor to have a significant effect on compensating same amount of glucose. For example, an IOB value of 5 units is enough to drop the blood glucose levels very quickly for a patient with 20 units TDD, but will not have the same effect (e.g., will not drop blood glucose levels very quickly) for a patient with 60 units TDD.

When the IOB value is not greater than the result (the "No" branch of 1006), the process 1000 determines that the condition indicating continuing hypoglycemia does not exist (step 1010). However, when the IOB value is greater than the result (the "Yes" branch of 1006), the process 1000 determines that there exists a condition indicating continuing hypoglycemia that continues when basal insulin delivery is suspended (step 1008). Here, the process 1000 determines that blood glucose levels decrease to a point below a "suspension threshold" (i.e., a threshold point at which the insulin delivery pump suspends basal insulin delivery). Due to a large IOB value detected by the process 1000, the process 1000 predicts the existence of a condition in which blood glucose levels will continue to decrease, thereby inducing hypoglycemia.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The following description refers to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Likewise, unless expressly stated otherwise, "connected" means that one element/node/feature is directly joined to (or directly communicates with) another element/node/feature, and not necessarily mechanically. Thus, although each of the schematics shown in FIGS. 1-6 depict one exemplary arrangement of elements, additional intervening elements, devices, features, or components may be present in an embodiment of the depicted subject matter.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A system for providing blood glucose data, the system comprising:
   an insulin delivery pump; and
   a controller comprising a system memory element and at least one processor, the controller communicatively coupled to the insulin delivery pump, and the controller configured to:
      cause suspension of a continuous basal insulin delivery by the insulin delivery pump prior to glucose levels falling into a hypoglycemic range;
      in response to the suspension of the continuous basal insulin delivery by the insulin delivery pump:
         predict that the suspension of the continuous basal insulin delivery will be insufficient to prevent the glucose levels from falling into the hypoglycemic range and thereby identify a condition in which the glucose levels will continue to decrease after the suspension of the continuous basal insulin delivery, wherein the controller is further configured to identify the condition by:
            obtaining an insulin on board (IOB) value, via the insulin delivery pump, wherein the IOB value is a quantity of insulin remaining in a body of a user following a bolus of insulin provided by the insulin delivery pump;
            scaling a total daily dose (TDD) value by a factor, to generate a result having a value that is less than the TDD value, wherein the TDD value is a quantity of insulin required by the user in a twenty-four hour period; and
            determining that the IOB value is greater than the result, wherein the condition comprises the IOB value being greater than the result; and
         initiate performance of an action by the insulin delivery pump, in response to identifying the condition in which the glucose levels will continue to decrease after the suspension of the continuous basal insulin delivery, for preventing the glucose levels from falling into the hypoglycemic range in combination with the suspension of the continuous basal insulin delivery.

2. The system of claim 1, wherein the controller is integrated into the insulin delivery pump, and wherein the system comprises a device including the controller and the insulin delivery pump.

3. The system of claim 1, wherein the controller is further configured to:
   identify a problematic glucose trend indicative of leading to hypoglycemic levels, via the insulin delivery pump, and
   wherein the suspension of the continuous basal insulin delivery is based on the problematic glucose trend.

4. The system of claim 1, wherein the controller is further configured to identify the condition by:
   calculating a glucose trend value, using the insulin delivery pump; and
   determining that the glucose trend value is less than a predetermined threshold that indicates hypoglycemia, wherein the condition further comprises the glucose trend value being less than the predetermined threshold, the condition indicating that blood glucose levels will continue to decrease when the continuous basal insulin delivery is suspended thereby inducing hypoglycemia.

5. The system of claim 4, wherein the insulin delivery pump is further configured to collect a plurality of sensor glucose values; and
   wherein the controller is further configured to calculate the glucose trend value by computing a derivative of the plurality of sensor glucose values, and wherein the glucose trend value comprises the derivative.

6. The system of claim 1, wherein the controller is further configured to initiate providing, by the insulin delivery pump, a glucagon injection, in response to identifying the condition, and wherein the action comprises providing the glucagon injection.

7. The system of claim 1, wherein the controller is further configured to present an alert comprising at least one of an audio alert and a visual alert, and wherein the action comprises presenting the alert.

8. The system of claim 1, wherein the glucose levels falling into the hypoglycemic range is a predicted hypoglycemic event, and wherein the condition indicates that the predicted hypoglycemic event will continue after the continuous basal insulin delivery is suspended.

9. The system of claim 8, wherein the condition indicating that the predicted hypoglycemic event will continue after the continuous basal insulin delivery is suspended also indicates that the predicted hypoglycemic event is not rectifiable by suspending the continuous basal insulin delivery.

10. The system of claim 8, wherein the action addresses the predicted hypoglycemic event.

* * * * *